(12) United States Patent
Lobanoff

(10) Patent No.: US 11,534,260 B2
(45) Date of Patent: Dec. 27, 2022

(54) NEAR INFRARED ILLUMINATION FOR SURGICAL PROCEDURE

(71) Applicant: Mark Lobanoff, North Oaks, MN (US)

(72) Inventor: Mark Lobanoff, North Oaks, MN (US)

(*) Notice: Subject to any disclaimer, the term of this patent is extended or adjusted under 35 U.S.C. 154(b) by 309 days.

(21) Appl. No.: 16/866,030

(22) Filed: May 4, 2020

(65) Prior Publication Data
US 2020/0345449 A1 Nov. 5, 2020

Related U.S. Application Data

(60) Provisional application No. 62/842,637, filed on May 3, 2019.

(51) Int. Cl.
| | | |
|---|---|---|
| *A61B 90/35* | (2016.01) | |
| *A61B 90/25* | (2016.01) | |
| *A61B 90/00* | (2016.01) | |
| *A61F 9/007* | (2006.01) | |
| *G03B 15/02* | (2021.01) | |
| *H04N 5/225* | (2006.01) | |

(52) U.S. Cl.
CPC .............. *A61B 90/35* (2016.02); *A61B 90/25* (2016.02); *A61B 90/361* (2016.02); *A61F 9/007* (2013.01); *G03B 15/02* (2013.01); *H04N 5/2256* (2013.01); *H04N 5/2257* (2013.01); *A61B 2090/366* (2016.02); *A61B 2090/372* (2016.02)

(58) Field of Classification Search
None
See application file for complete search history.

(56) References Cited

U.S. PATENT DOCUMENTS

2017/0280989 A1* 10/2017 Heeren .................... A61B 3/14
2018/0360655 A1* 12/2018 Berlin .................... A61B 34/20

FOREIGN PATENT DOCUMENTS

DE     102015202772 A1    8/2016

* cited by examiner

*Primary Examiner* — Kaitlin A Retallick
(74) *Attorney, Agent, or Firm* — Christensen, Fonder, Dardi & Herbert PLLC; Peder Jacobson

(57) ABSTRACT

Systems, devices, and methods for surgical illumination and imaging of ophthalmologic structures within a human eye are disclosed. In various embodiments, an emitter, imaging sensor, and a system control image processor are configured to irradiate ophthalmologic structures with near infrared light, detect near-infrared scatter from the irradiated ophthalmologic structures and visible light in real-time and generate or otherwise cause an image to be displayed on the user display that includes the detected near-infrared scatter from the irradiated ophthalmologic structures displayed in real-time. In one or more embodiments, the image is a virtual image of the irradiated ophthalmologic structures generated at least based on near-infrared light scattering coefficients of the irradiated ophthalmologic structures. In certain embodiments, the image displayed on the user display includes the detected near-infrared scatter from the irradiated ophthalmologic structures overlaid on a real-time view from a surgical microscope.

20 Claims, 10 Drawing Sheets

NEAR INFRARED ILLUMINATION FOR SURGICAL PROCEDURE

RELATED APPLICATIONS

The present application claims the benefit of U.S. Provisional Patent Application No. 61/842,637, filed May 3, 2019, the disclosure of which is incorporated by reference herein in its entirety.

FIELD OF THE DISCLOSURE

The present disclosure relates to ophthalmic surgical procedures. More specifically, the present disclosure relates to the use of infrared light for illuminating structures of the eye during an ophthalmic surgical procedure.

BACKGROUND

Glaucoma is a disease affecting the eyeball that generally results in an elevation of intraocular pressure within the eye. There are two major types of glaucoma, open angle glaucoma, and closed angle glaucoma. Open angle glaucoma, the most common type of glaucoma, occurs when the normal appearing outflow pathways malfunction such that the eye does not adequately drain aqueous fluid. Under ordinary function, the aqueous fluid drains through Schlemm's canal, a vessel that delivers the aqueous to blood vessels via aqueous veins. The portion of the canal nearest to the anterior chamber is covered by the trabecular meshwork. The meshwork is a layer of tissue around the base of the cornea that normally allows the aqueous to drain into Schlemm's canal.

Elevated intraocular pressure in most open-angle glaucoma is due to an obstruction of aqueous outflow localized predominantly at the trabecular meshwork and the inner wall of Schlemm's canal. This change in intraocular pressure may present suddenly or may increase gradually over time. If left untreated, glaucoma may result in damage to the optic nerve and vision loss.

Treatments for elevated intraocular pressure due to outflow obstruction include topical and systemic medications, office-based laser procedures, and surgical procedures—including the commonly termed minimally invasive glaucoma surgery (MIGS), or micro-invasive glaucoma surgical procedures. Current approaches of intraocular pressure reduction by MIGS include increasing trabecular outflow by bypassing the outflow obstruction and enable resumption of flow via the eye's intrinsic outflow system which is often intact and functional beyond the region of outflow obstruction, rather than creating alternative pathways which may have significantly greater short and/or long term risks.

MIGS procedures often involve visualization of the outflow structures of the eye, especially those that reside beyond the "critical angle" of the optical pathway. Due to the shape of the cornea and the location of intraocular structures related to MIGS procedures in the region where the iris appears to meet the peripheral cornea, total internal reflection occurs and can prevent a surgeon from viewing those outflow structures that reside beyond the "critical angle" of the optical pathway. Even when using a prism on the cornea, which allows one to overcome the critical angle and view periphery of the anterior chamber, it can be difficult to detect the true location of the trabecular meshwork. Furthermore, using standard microscopy, it is difficult to detect the aqueous veins. Considering the above, it would be helpful to have improved methods and apparatus for viewing/imaging the eye during surgical procedures, targeting outflow structures of the eye such as Schlemm's canal and the aqueous draining veins, and determining target locations for openings through the trabecular meshwork and into Schlemm's canal to improve flow.

SUMMARY

Various embodiments of the disclosure are directed to systems for surgical illumination and providing improved visualization/identification of structures within an eye during ophthalmic surgical procedures. One or more embodiments provide advantageous improvements to available systems/technologies for performing minimally invasive glaucoma surgery (MIGS). For example, one or more embodiments of the disclosure provide benefits in the form of a system configured to provide real-time true images of ophthalmic structures of the eye, as opposed to an image derived from mathematical calculations or represented by OCT. In addition, various embodiments provide benefits in a system that is relatively low cost and utilizes near-infrared light but can identify deep structures within the eye such as aqueous veins and/or the trabecular meshwork. As such, various embodiments allow for visualization of outflow structures in the eye that are often necessary for a surgeon to best perform MIGS procedures. Such embodiments provide a distinct improvement over both known direct and indirect viewing tools—which can require significant dexterity and a steep learning curve.

As used herein, the term illumination of tissue refers to both illuminating an area, such as an operating field, from a light source that is located some distance away from the tissue and to transillumination, where a light source is located against or very near the tissue of the eye and light passes through physical material of the eye to light various structures therein.

In one or more embodiments, the system includes an optical microscope; an emitter configured to irradiate the ophthalmologic structures with near-infrared (NIR) light; an imaging sensor configured to receive at least near infrared light; and an image display apparatus. In embodiments, the imaging sensor may be configured to receive visible light in addition to NIR light. In embodiments, a second imaging sensor may be configured to receive visible light. In embodiments, the image display apparatus may include a processor, an electronic storage location operatively coupled with the processor, and processor executable code stored on the electronic storage location and embodied in a tangible non-transitory computer readable medium. In embodiments, the processor executable code may include machine-readable instructions, that when executed by the processor, causes a near infrared eye image to be displayed in real-time as detected by the imaging sensor. In embodiments, the near infrared eye image includes the ophthalmologic structures as captured by the imaging sensor. In embodiments, the near infrared image is displayed directly through the oculars of the surgical microscope.

In embodiments, a pathway is created by inserting a stent in the ophthalmologic structures. In embodiments, a pathway is created by inserting a MIGS device in the ophthalmologic structures. In embodiments, a MIGS device includes a stent. In embodiments, a MIGS device includes a shunt. In embodiments, the ophthalmologic structures include a trabecular meshwork. In embodiments, the ophthalmologic structures include Schlemm's canal. In embodiments, the ophthalmologic structure includes an anterior chamber. In embodiments, the ophthalmologic structure includes one or more aqueous veins.

In embodiments, the emitter illuminates the trabecular meshwork and the aqueous veins. In embodiments, the near infrared eye image is overlaid on a view from the surgical microscope. In embodiments, the image display apparatus includes a heads-up display (HUD) permitting a surgeon to view the near infrared image. In embodiments, the near infrared eye image is projected onto eye.

A method of performing minimally invasive glaucoma surgery on an eye includes providing a system for performing minimally invasive glaucoma surgery; illuminating the ophthalmologic structures with near infrared light; viewing the ophthalmologic structures with the optical microscope; and identifying a trabecular meshwork. The method may further include displaying a view from the surgical microscope on a heads-up display (HUD). The method further includes displaying the near infrared image of the eye on a HUD. The method may further include overlaying the near infrared image of the eye on the view from the surgical microscope. The method may further include projecting the near infrared image of the eye onto the eye. The method may further include inserting a MIGS device from a first side of the trabecular meshwork abutting an anterior chamber of the eye to an opposite side of the trabecular meshwork, such that a fluid may flow between the anterior chamber and the opposite side of the trabecular meshwork.

In embodiments, a MIGS device may be between 0.5 and 3 mm in length. In embodiments, a MIGS device may be about 1 mm in length. In embodiments a MIGS device is between 0.2 and 1.0 mm in height. In embodiments, a MIGS device is 0.33 mm in height. In embodiments, NIR light has a wavelength between 550 and 1550 nanometers. In embodiments, NIR light has a wavelength between 400 and 1000 nanometers. In embodiments, NIR light has a wavelength between 650 and 1050 nanometers.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

Figure 1:
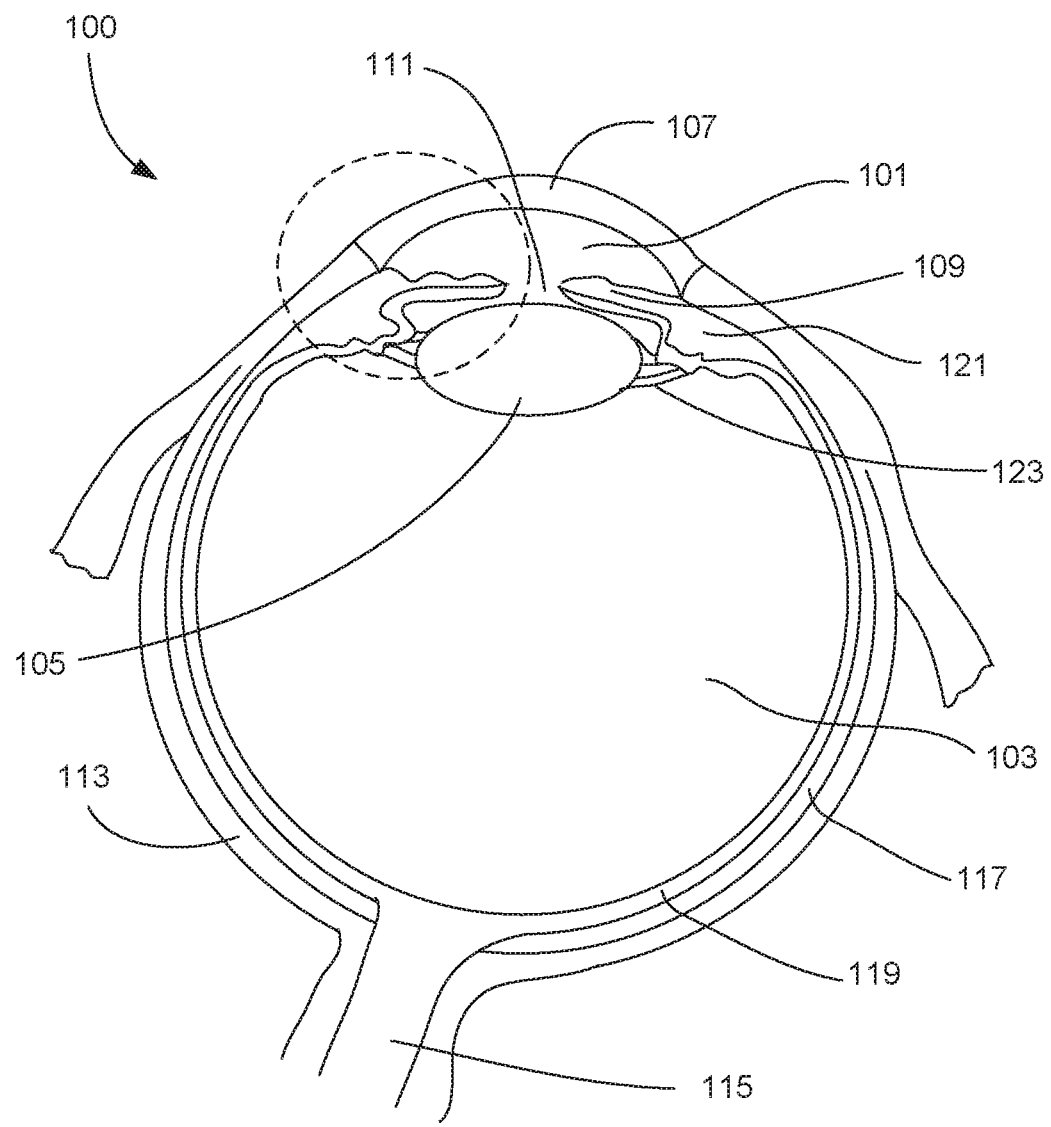
FIG. 1 depicts a cross-sectional view of an eye according to one or more embodiments of the disclosure.

While the embodiments of the disclosure are amenable to various modifications and alternative forms, specifics thereof have been shown by way of example in the drawings and will be described in detail. It should be understood, however, that the intention is not to limit the disclosure to the embodiments described. On the contrary, the intention is to cover all modifications, equivalents, and alternatives falling within the spirit and scope of the disclosure.

DETAILED DESCRIPTION

Figure 2:
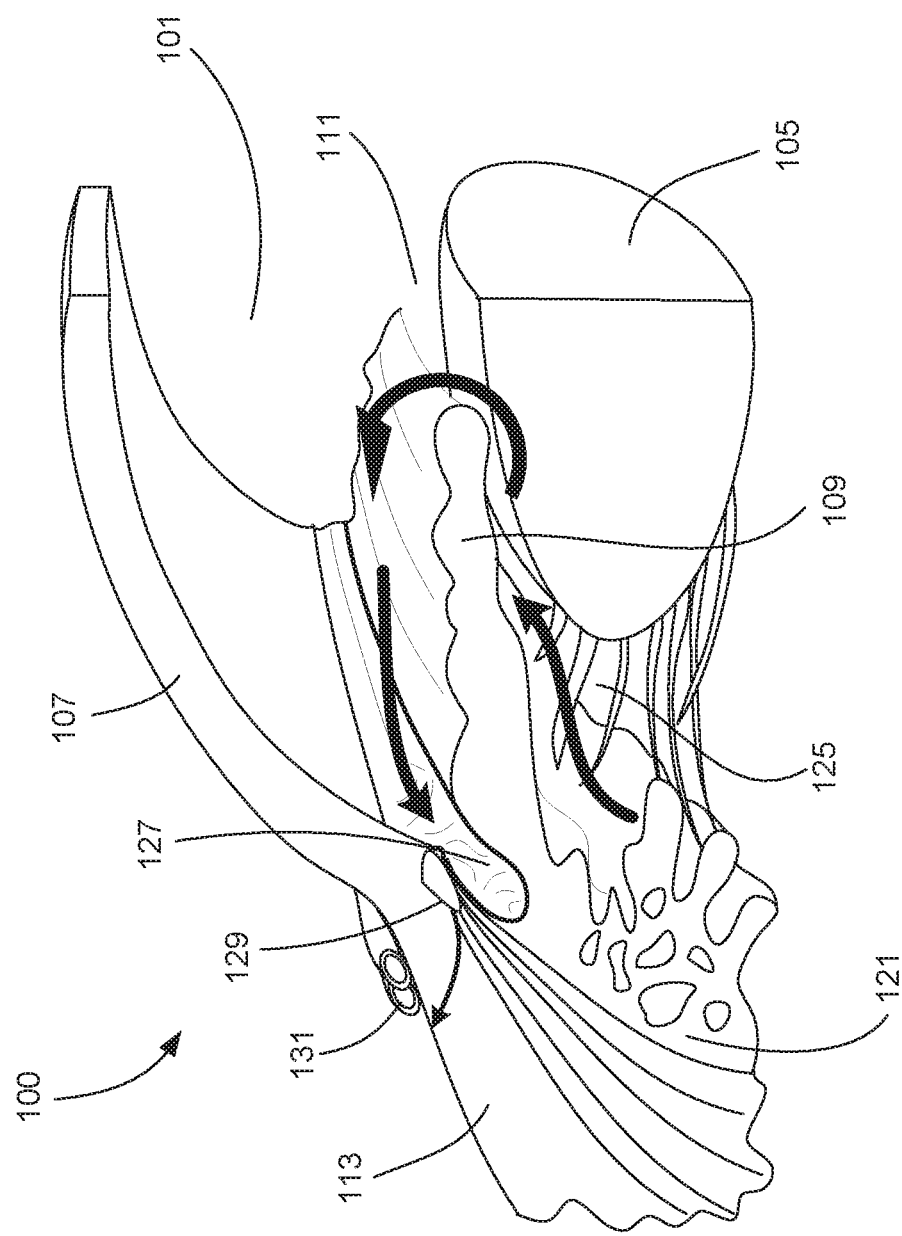
FIG. 2 depicts a partial cross-sectional view of the portion of the eye outlined in dashed lines in FIG. 1 according to one or more embodiments of the disclosure.

Referring to FIG. 1-2, a cross-sectional view of an eye 100 is shown having an anterior chamber 101 and a posterior cavity 103. The anterior chamber 101 is located between a lens 105 and the cornea 107. The iris 109 forms an annulus above then lens 105, where the pupil 111 is the open center portion of the iris 109. The sclera 113 surrounds the eye, extending from the lens 105 to the optic nerve 115. The sclera 113 further surrounds the choroid 117 and the retina 119. Suspensory ligaments 123 secure the lens to ciliary body 121.

The anterior chamber 101 contains aqueous humor. Aqueous humor is a transparent, watery fluid secreted by ciliary body 121. Aqueous humor serves several functions in the eyeball, such as maintaining hydrostatic pressure that keeps the eye in its generally spherical shape. Ciliary body 121 continually produces aqueous humor in the posterior chamber 125 between the lens 105 and iris 109. As shown in FIG. 2, the continually secreted aqueous humor follows a flow path between lens 105 and iris 109, through the pupil 111 into the anterior chamber 101, around the top surface of the iris 109 and towards the portion of the anterior chamber 101 where the cornea 107, sclera 113, and iris 109 converge. The trabecular meshwork 127 is located near this juncture. The trabecular meshwork includes three structural areas: the inner uveal meshwork, the corneoscleral meshwork, and the juxtacanalicular (JCT). The JCT is immediately adjacent to Schlemm's canal. In a normally functioning eye, the trabecular meshwork 127 allows aqueous humor to pass through the meshwork 127 and into Schlemm's Canal 129. The fluid then continues through aqueous veins and can drain into other vessel systems in the eye such as episcleral vessels 131. This flow rate is timed with the production of aqueous humor such that there is a generally stable intraocular pressure maintained with the eye. Inflow and outflow of a healthy eye are generally about 2.75 µL/minute. Aqueous veins eventually join episcleral vessels containing blood. Aqueous veins may discharge small amounts of blood. As aqueous veins approach episcleral vessels, the veins may have varying amounts of blood and aqueous humor. The locations at which blood and aqueous mix, as well as the rate of flow, may be related to intraocular pressure within the eye.

In a diseased eye, such as one affected by glaucoma, the trabecular meshwork 127 does not permit the aqueous humor to easily pass through into Schlemm's Canal 129. The ciliary body 121, however, continues to produce and fill posterior and anterior chambers with aqueous humor. The continuous production of aqueous humor thereby causes an increase in pressure in the anterior chamber 101. This pressure will then exert downward force on posterior cavity 103. If left untreated, the downward force exerted on posterior cavity 103 will impact optic nerve 115. In some cases, the impact on optic nerve 115 may result in blindness or other vision impairments.

Surgical procedures may be used to relieve intraocular pressure in the anterior chamber 101. For example, surgery aimed at the ciliary body 121 might be designed to reduce or stop the output of aqueous humor. However, it may be difficult to precisely alter the production of aqueous humor such that intraocular pressure is properly maintained in the eye.

Figure 3:
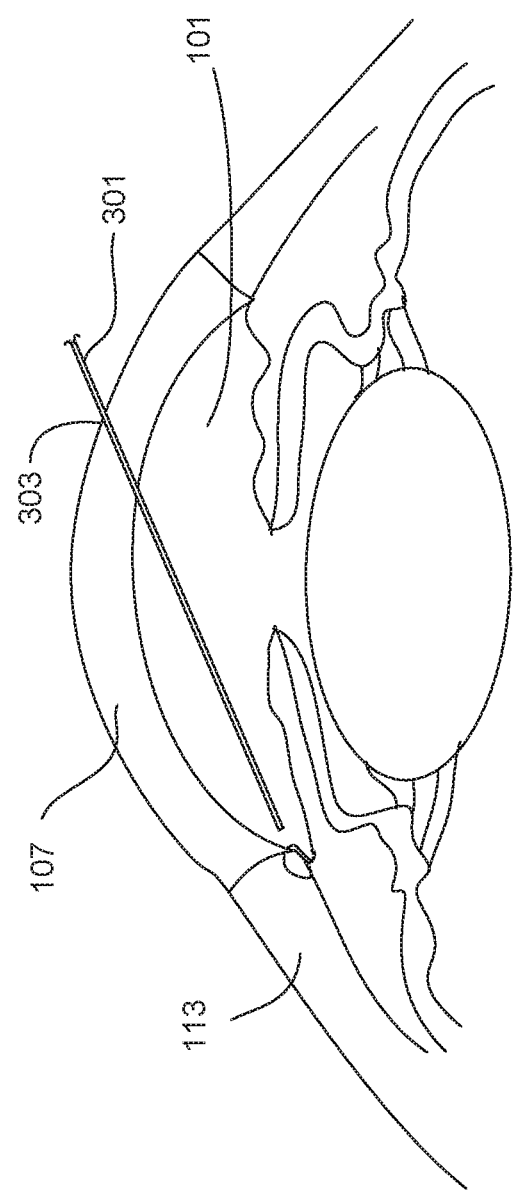
FIG. 3 depicts a cross-sectional view of a surgical tool crossing the anterior chamber of an eye according to one or more embodiments of the disclosure.

One surgical option is minimally invasive glaucoma surgery (MIGS). MIGS procedures generally avoid trauma to the sclera 113 and other tissues. As seen in FIG. 3, a MIGS procedure can involve inserting a surgical tool or probe 301 into anterior chamber 101 through cuts or micro-incisions 303 in the cornea 107. Such procedures can be advantageous as corneal incisions 303 generally result in less discomfort and more rapid healing than cutting through either other tissues or structures of the eye 100.

Figure 4:
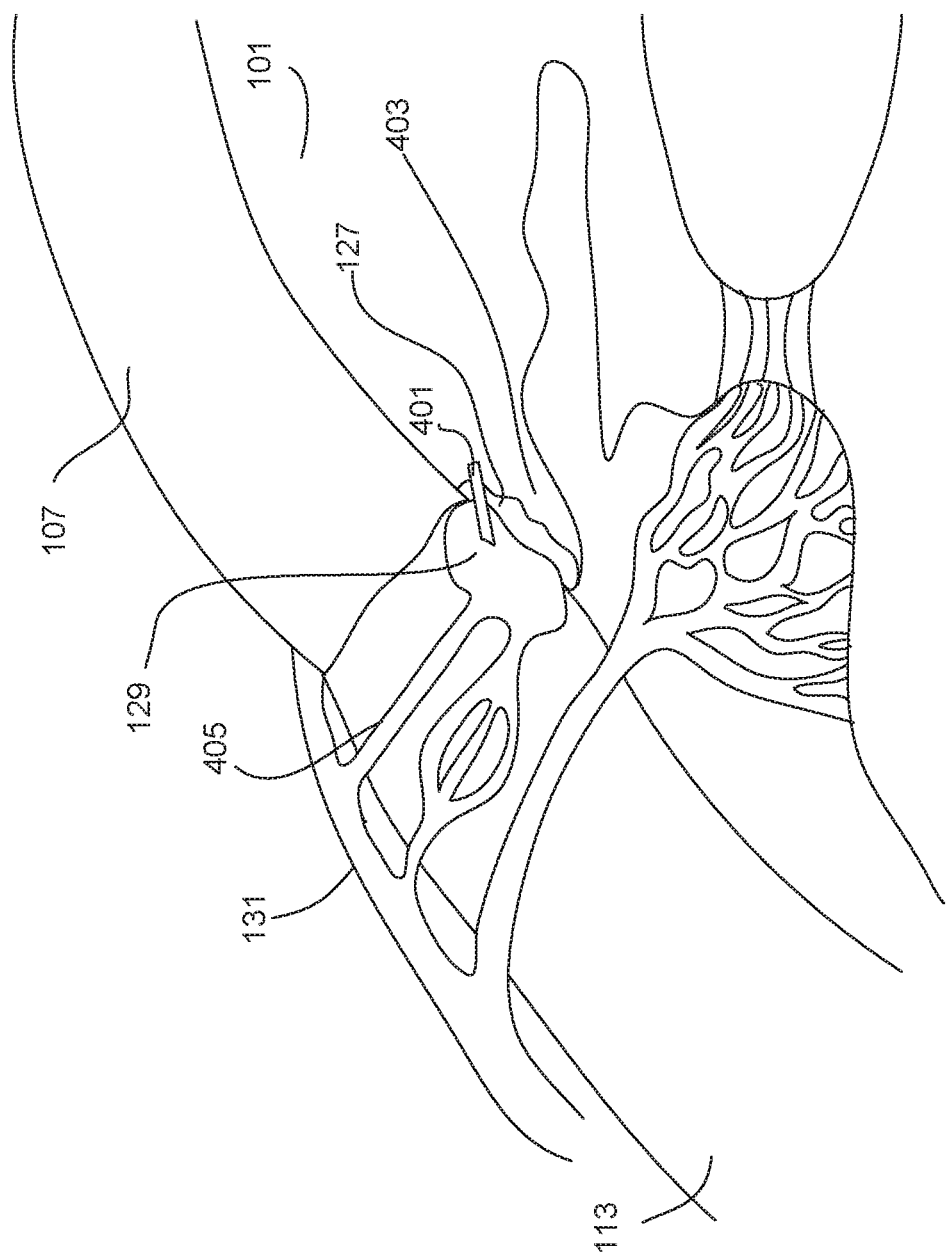
FIG. 4 depicts an enlarged cross section of a portion of the anterior chamber of an eye with a stent bridging the trabecular meshwork according to one or more embodiments of the disclosure.

Referring to FIG. 4, a MIGS device 401 is depicted inserted into the eye 100. In various embodiments, MIGS device 401 may be a shunt. In one or more embodiments, MIGS device 401 may be a stent. In certain embodiments, MIGS device 401 may be between 0.5 and 3 mm in length. In one or more embodiments, MIGS device 401 may be about 1 mm in length. MIGS device 401 may be inserted through the trabecular meshwork 127 to create a pathway between anterior chamber 101 and Schlemm's canal 129. When the regular flow of aqueous humor is impeded, such as in an eye affected by glaucoma, the MIGS device 401 can improve flow by creating a pathway for aqueous humor to flow from anterior chamber 101, through the MIGS device 401 bypassing the impediment, and into Schlemm's canal 129. By creating a pathway for aqueous humor to drain from anterior chamber 101, the MIGS device 401 can improve intraocular pressure and help to prevent permanent damage to optic nerve 115.

Given the small dimensions of the ophthalmologic structures in the eye, and the obscured location of the trabecular meshwork 127 in an angle 403 of the anterior chamber 101, it can be difficult for a surgeon to position and place the MIGS device 401 in the proper location. As such, a surgeon may use image enhancement techniques, such as surgical microscopes, to provide improved images of the surgical field.

Figure 5:
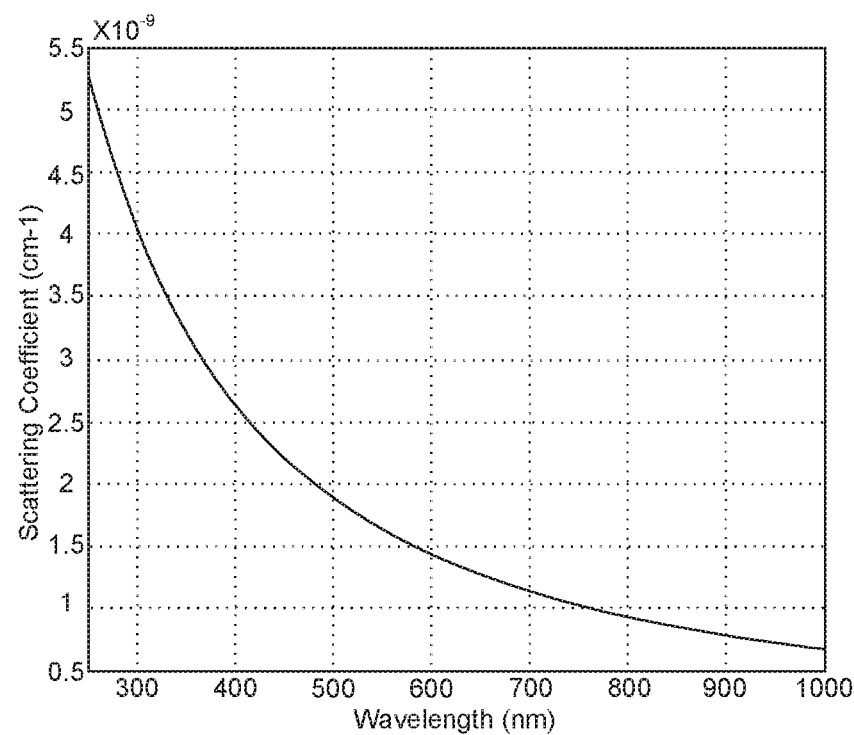
FIG. 5 depicts the molar extinction coefficients of oxygenated and unoxygenated hemoglobin at various wavelengths of light.

In one or more embodiments, one such technique involves the use of infrared or near-infrared (NIR) light. For example, described further below, one or more embodiments are directed to a MIGS imaging system capable of identifying ophthalmologic structures within an eye for creating a fluid pathway. Described further below in various embodiments the MIGS imaging system includes a surgical microscope, an emitter configured to irradiate ophthalmologic structures NIR light, and an imaging sensor configured to receive and detect one or more NIR light and visible light, and an image display apparatus that causes an image of the eye, with ophthalmologic structures illuminated via near infrared light, to be displayed in real-time on the display wherein the near infrared eye image includes the ophthalmologic structures captured by the imaging sensor. As referred to herein, NIR light includes light possessing a wavelength between and including 550 and 1550 nanometers. While most visible light is reflected off skin and tissue, NIR light can penetrate tissue up to several centimeters in depth making it particularly useful for surgical imaging. For example, FIG. 5 shows the scattering coefficient of tissue at various wavelengths of light.

Figure 6:
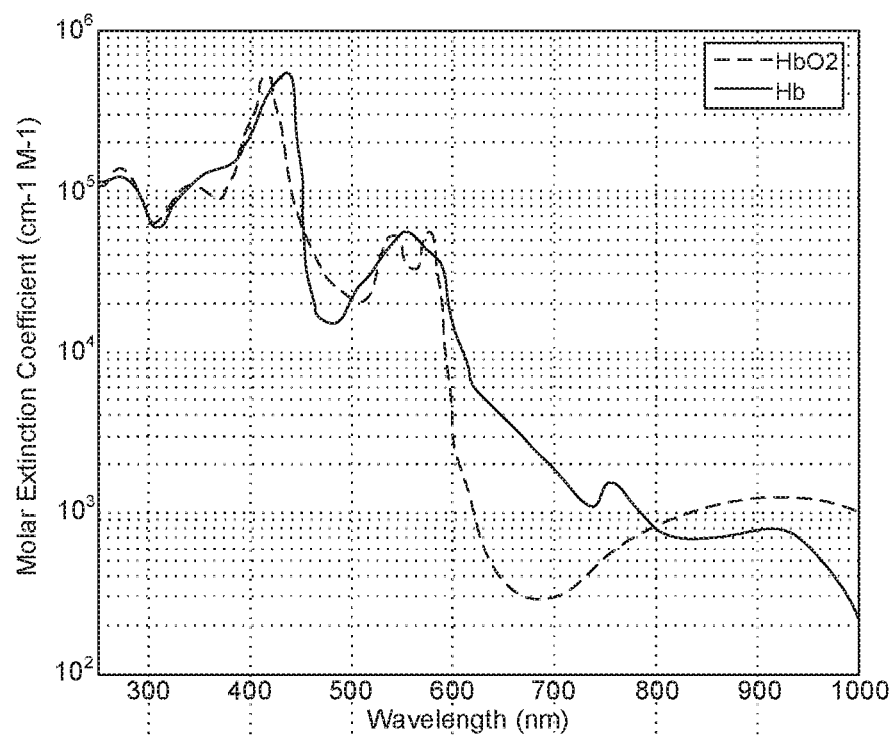
FIG. 6 depicts the scattering coefficient at various wavelengths of light.

Some elements in the body more readily absorb NIR light at certain frequencies. For example, oxygenated and deoxygenated hemoglobin in the bloodstream have peak absorptions at different frequencies. As an example, FIG. 6 illustrates the molar extinction coefficient of both oxygenated and unoxygenated hemoglobin at various wavelengths of light. The molar extinction coefficient is correlated to the absorption coefficient of photon absorption in tissue. This makes it possible to identify veins, arteries, and other tissue beneath the skin by directing NIR light at those structures. The diffuse spectrum of NIR light causes the light to spread over a larger area, eliminating the need for more point specific probes. In the case of MIGS, a surgeon can generally direct NIR light at the eye such that it illuminates an area that can include the trabecular meshwork, Schlemm's canal, aqueous veins, and other important structures pertaining to the surgery. In various embodiments NIR light focused towards the trabecular meshwork can make the structure more readily identifiable via absorption and allows a surgeon to quickly and accurately implant a MIGS device. Speed and accuracy in surgery can decrease a patient's discomfort while speeding recovery time and yielding better outcomes, such as restoring flow patterns of aqueous humor.

Figure 7:
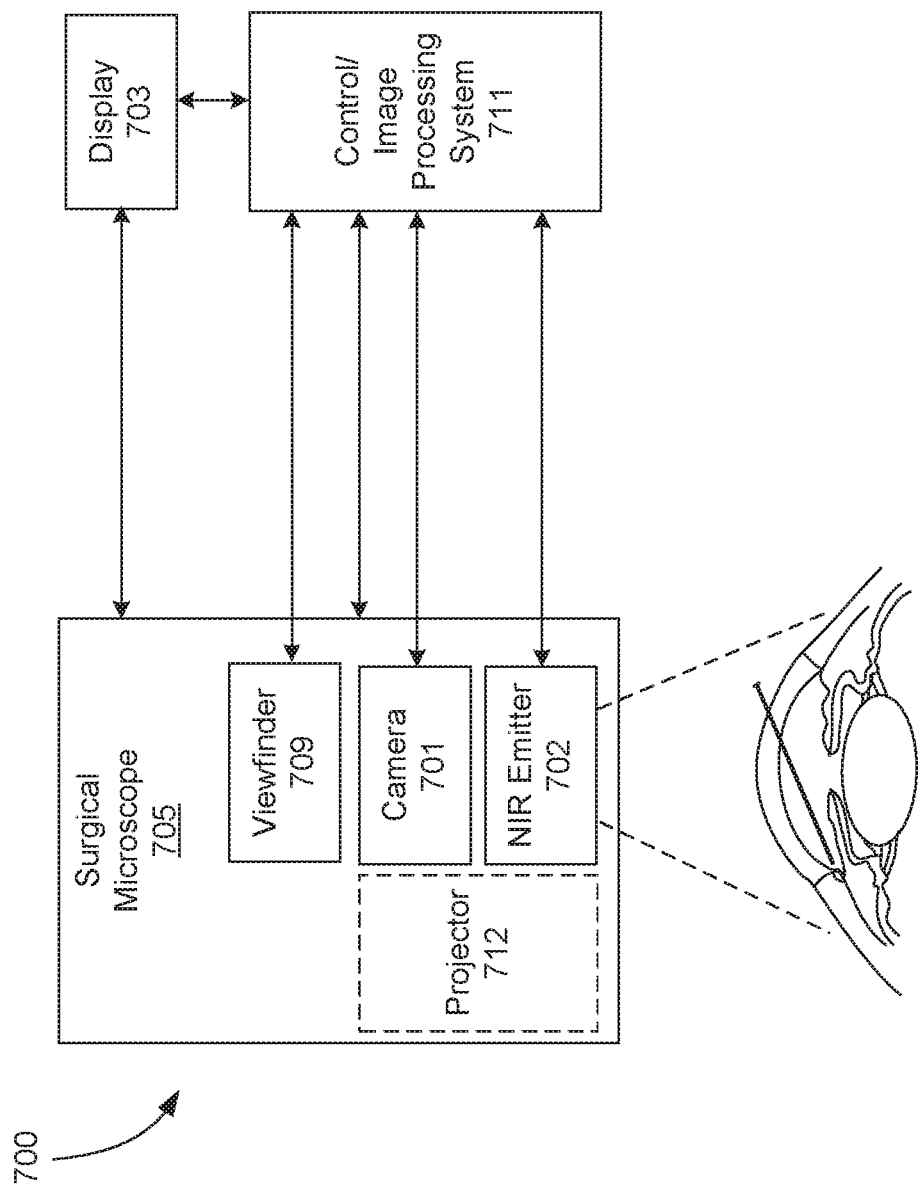
FIG. 7 depicts a system for ophthalmic surgical illumination according to one or more embodiments of the disclosure.

FIG. 7 depicts a surgical illumination and imaging system 700 for providing improved visualization/identification of structures within an eye during ophthalmic surgical procedures, such as for use in minimally invasive glaucoma surgery. In one or more embodiments, the system 700 includes a camera 701, an NIR emitter 702, a display 703, a surgical microscope 705, a viewfinder, 709, and a computer control and image processing system 711.

In one or more embodiments, the camera 701, is an optical sensor configured to detect and record light in the NIR spectrum. In addition to the NIR spectrum, the camera 701 may be configured to detect light in the visual spectrum or other spectrums in addition to detecting NIR light. In one or more embodiments, the emitter 702 is an LED or other light source that is configured to produce and direct NIR light towards a patient. The NIR emitter 702 may be a standalone component, or it may be integrated into other surgical system components such as those described herein. For example, in one or more embodiments the camera 701 may be configured with the NIR emitter 702 as an integrated component of the system 700.

In one or more embodiments the surgical microscope 705 is an optical or other type of microscope instrument configured to view the operating field and output a magnified image of the observed field for use in a surgical procedure. In one or more embodiments the viewfinder 709 is a component of the microscope 705 and allows a surgeon to see the observed operating field. In various embodiments, viewfinder 709 may be monocular or stereoscopic. In certain embodiments, the viewfinder may be a digital display that displays the observed operating field in real-time. In various embodiments, one or more of the camera 701 and emitter 702 may be integrated with the surgical microscope 705 as a combined component of the system 700, such as depicted in FIG. 7. However, in certain embodiments, some or all the elements of the system 700 could be individual components.

In various embodiments, the computer control and image processing system 711 is a collection of processing and memory components that are communicatively coupled with, directly or indirectly, each of the elements of the system 700 for user control of system elements, input and output of data, and other functions. As such, in various embodiments the control system 711 can include a processor; memory; internal or external network interface or communications devices (e.g., modem, network interface cards); optional input devices (e.g., a keyboard, mouse, touchscreen, or other input device); and commercially available or custom software (e.g., a graphical user interface (GUI) for receiving commands and outputting data to users, browser software, communications software, server software, natural language processing software, search engine and/or web crawling software, filter modules for filtering content based upon predefined criteria). In various embodiments the control system 711 is equipped with an output device such as the display 703. In one or more embodiments, the display 703 is configured as a surgical heads-up device (HUD) that presents information, video, images, or other content from various elements of the system 700 to the surgeon. In one or more embodiments the camera 701, NIR emitter 702, and viewfinder 709 are coupled with or networked with the control system 711 to define the overall system 700.

In operation, the NIR emitter 702 is configured to begin emitting light toward an observed operating field, which depicted in FIG. 7 is shown for example as a cross section of an eye undergoing a MIGS procedure. The NIR camera 701 is positioned generally to detect NIR light that is emitted via the NIR emitter 702 directed towards the eye. For example, the NIR camera 701 may be positioned directly over a patient laying prone on a surgical bed 707. In one or more embodiments, the camera 701 detects scattered NIR light and transfers this image to the computer system 711, surgical microscope 705, or both. The control system 711, in turn, may generate a virtual image based on the NIR image received from the NIR camera 701. The image is subsequently presented to a user via the display 703 for use in surgery. Because various types of ophthalmic tissue possess different scattering coefficients, the control/image processing system can analyze the input images from the camera 701 to distinguish various tissue. In such embodiments, the virtual image can identify or display a representation of one or more of the trabecular meshwork 127, Schlemm's canal 129, aqueous veins 405, or other ophthalmologic structures to accurately and clearly display such structures to a user. In addition, in various embodiments, the virtual image is continuously updated and presented based on real-time data from the camera 701 and emitter 702 to create a real-time virtual representation of the illuminated tissue. In embodiments, the virtual image may be overlaid atop a visible light image captured by a surgical microscope 705 or another camera, creating a hybrid image. In embodiments, the computer system 711 overlays the virtual image onto the visible light image. In embodiments, the computer system 711 outputs the hybrid image onto the display 703. In this manner, a surgeon can readily see the eye, the surgical tools and implements such as MIGS devices, and the ophthalmologic structures on the display 703 in real-time while performing the MIGS.

In various embodiments, the computer system 711 may overlay the virtual image into the field of view of a surgical microscope in the image presented on the display 703. In this manner, a surgeon can readily see the eye, the surgical tools and implements such as MIGS devices, and the ophthalmologic structures when looking through viewfinder 709. In various embodiments, the computer system 711 may project the virtual image onto a patient's eye using a projector 712. In such embodiments, the surgical microscope 705 include a projector. In this manner, a surgeon can readily see the eye, the surgical tools and implements such as MIGS devices, and the ophthalmologic structures when looking directly at the operation field.

One skilled in the art will recognize that the surgical system described above may have uses for procedures other than inserting devices into the eye. For example, surgical system 700 may be used in alternative surgical glaucoma treatments such as trabeculectomies and electrocauteries. The surgical system may also allow better visualization of the anterior lens capsule in dense cataracts, making capsulorrhexis formation during cataract surgery easier and safer. Although the steps of other eye surgeries are not described in detail, the use of surgical system 700 to perform other surgeries on the eye is not beyond the scope of this disclosure.

Figure 8:
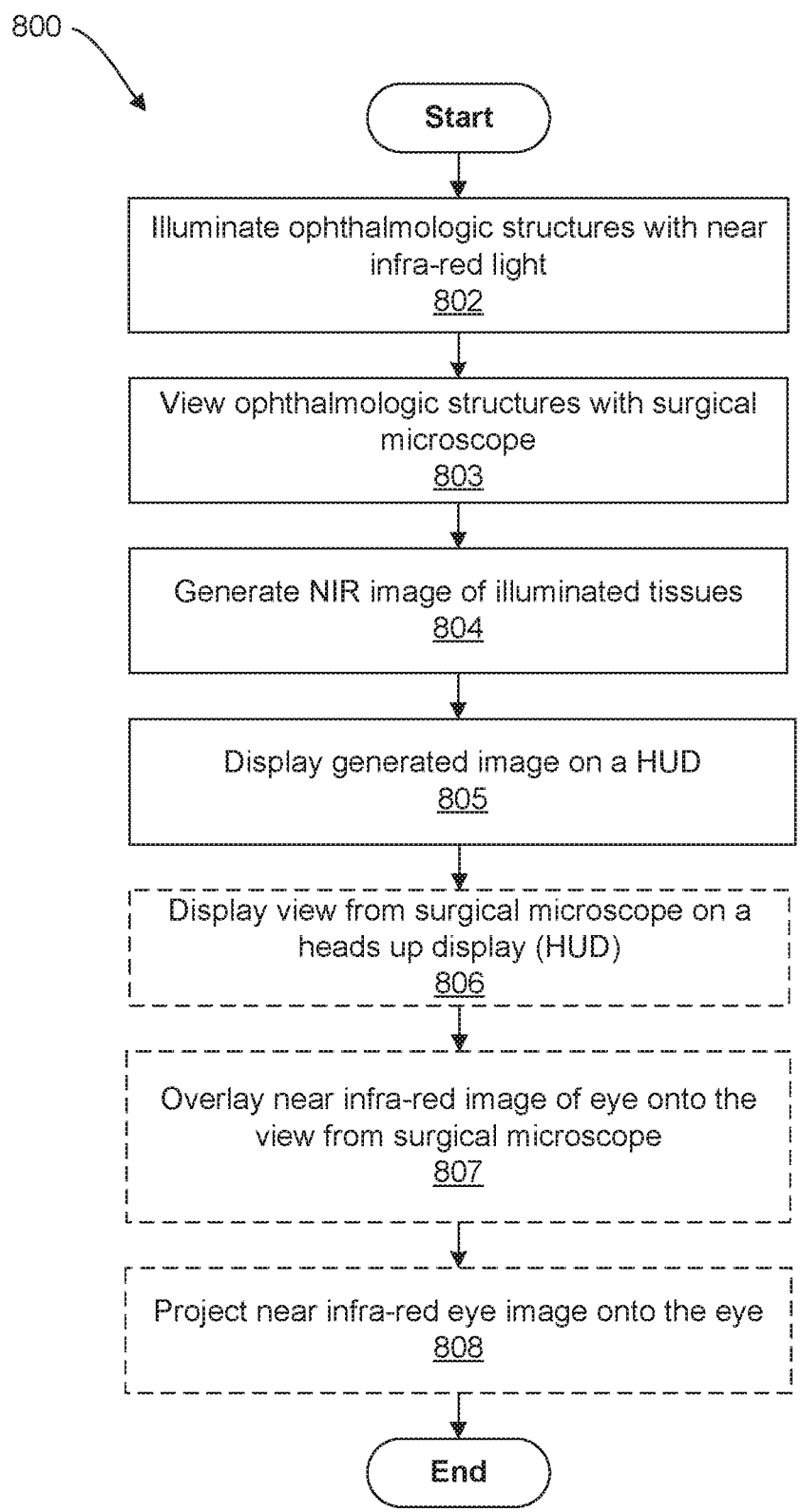
FIG. 8 depicts a flowchart diagram of a method for ophthalmic surgical illumination, according to one or more embodiments of the disclosure.

FIG. 8 illustrates a flowchart of a method 800 for a method of illuminating and imaging ophthalmic structures of the eye. The method 800 may use any of the embodiments of systems disclosed herein. As such, in various embodiments, at operation 802 near infrared light is used to illuminate ophthalmologic structures within the eye. In one or more embodiments, at operation 803 the ophthalmologic structures are viewed with a surgical microscope. As described above, in various embodiments, the surgical microscope can include a camera or other image sensor configured to detect and record light in the NIR spectrum. In addition to the NIR spectrum, the camera may be configured to detect light in the visual spectrum or other spectrums in addition to detecting NIR light. In various embodiments, because of the variable scattering coefficient of different types of tissue, the camera will pick up varying amounts of scattered NIR light from illuminated tissue. In operation 804, data from the camera is sent to and processed by the control/image processing system in real-time to construct a real-time virtual image representing and indicating the various tissues based on the NIR scatter. In operation 805 the generated image may be shown on a display such as a HUD such that a surgeon can view the real-time image depicting the location of the structures of the eye. Optionally, in operation 806 the view from the surgical microscope is shown on a display or monitor such as a heads-up display. Optionally, in one or more embodiments, at operation 807 a near infrared image of the eye may be overlaid onto the view from the surgical microscope such that the image creates a hybrid image depicting the identified tissue and their relative positions in the standard magnified image of the operating field. Optionally, in various embodiments, at operation 808 a near infrared image of the eye may be projected onto the patient's eye. Once illuminated and displayed for a user a MIGS device may more easily and accurately inserted from a first side of the trabecular meshwork abutting an anterior chamber of the eye to an opposite side of the trabecular meshwork, such that a fluid may flow between the anterior chamber and the opposite side of the trabecular meshwork. One skilled in the art will recognize that some steps may occur in a different order than presented, and some steps may occur simultaneously, or nearly simultaneously as other steps described.

Figure 9:
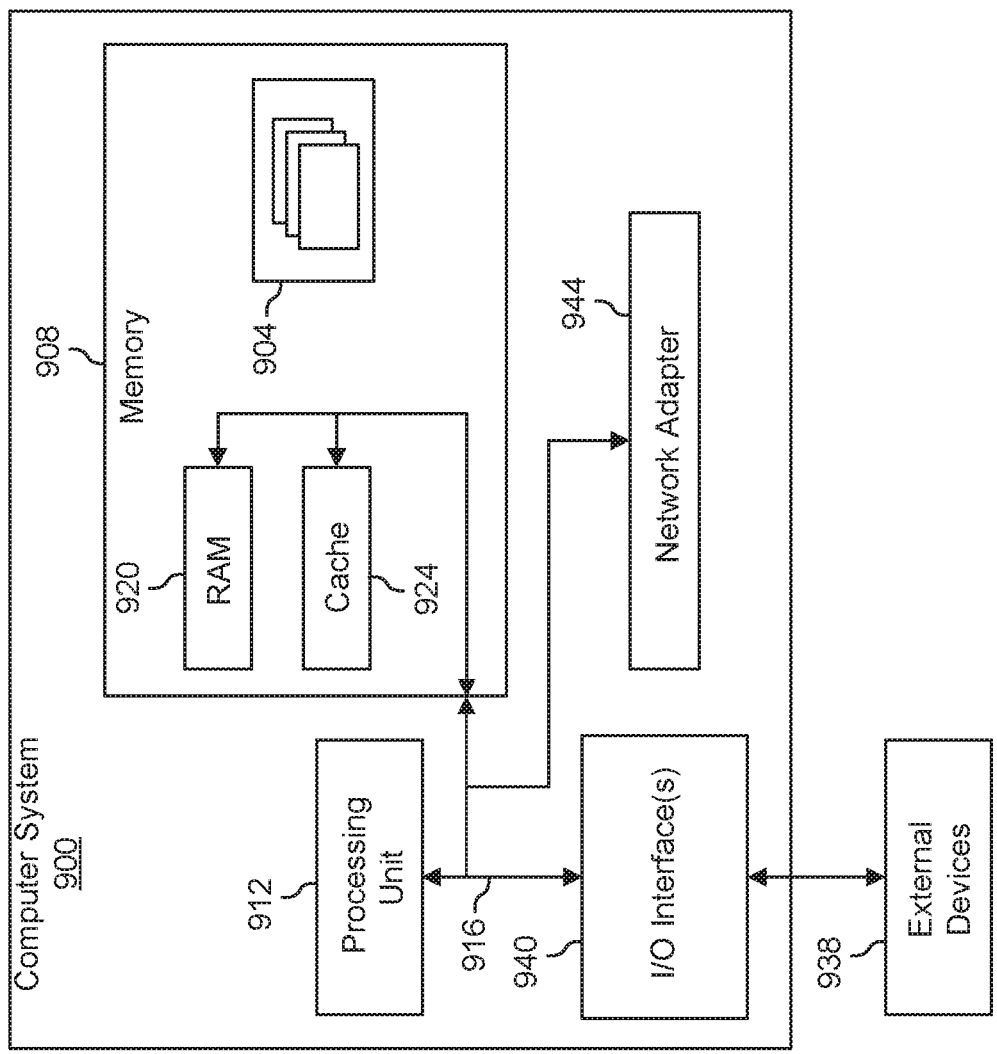
FIG. 9 depicts a computer system including a processor and a computer readable storage unit are depicted, according to one or more embodiments of the disclosure.

Referring to FIG. 9, a computer system 900 including a processor and a computer readable storage unit are depicted, according to one or more embodiments of the disclosure. In various embodiments computing system 900 is for use in surgical systems for providing improved visualization/identification of structures within an eye during ophthalmic surgical procedures, such as described in FIG. 7 above. As a result, computer system 900 can be configured to execute and/or store various program instructions as a part of a computer program product. Computer system 900 may be operational with general purpose or special purpose computing system environments or configurations, such as those described according to one or more of the embodiments herein.

Examples of computing systems, environments, and/or configurations that may be suitable for use with computer system 900 include, but are not limited to, personal computer systems, server computer systems, handheld or laptop devices, multiprocessor systems, mainframe computer systems, distributed computing environments, and the like.

Computer system 900 may be described in the general context of a computer system, including executable instructions, such as program modules 904, stored in system memory 908 being executed by a processor 912. Program modules 904 may include routines, programs, objects, instructions, logic, data structures, and so on, that perform particular tasks or implement particular abstract data types. Program modules 904 may be practiced in distributed computing environments where tasks are performed by remote processing devices that are linked through a network. In a distributed computing environment, program modules 904 may be located in both local and remote computer system storage media including memory storage devices. As such, in various embodiments computer system 900 can be configured to execute various program modules 904 or instructions for executing various embodiments of the disclosure.

The components of the computer system 900 may include, but are not limited to, one or more processors 912, memory 908, and a bus 916 that couples various system components, such as, for example, the memory 908 to the processor 912. Bus 916 represents one or more of any of several types of bus structures, including, but not limited to, a memory bus and/or memory controller, a peripheral bus, and a local bus using a suitable of bus architecture.

In one or more embodiments, computer system 900 includes a variety of computer readable media. In one or more embodiments, computer readable media includes both volatile and non-volatile media, removable media, and non-removable media.

Memory 908 may include computer readable media in the form of volatile memory, such as random-access memory (RAM) 920 and/or cache memory 924. Computer system 900 may further include other volatile/non-volatile computer storage media such as hard disk drive, flash memory, optical drives, or other suitable volatile/non-volatile computer storage media. As described herein, memory 908 may include at least one program product having a set (e.g., at least one) of program modules 904 or instructions that are configured to carry out the functions of embodiments of the disclosure.

Computer system 900 may also communicate with one or more external devices 938 such as other computing nodes, a display, keyboard, or other I/O devices, via an I/O jinterface(s) 940 for transmitting and receiving data, instructions, or other information to and from the computer system 900. In one or more embodiments I/O interface 940 includes a transceiver or network adaptor 944 for wireless communication. As such, in one or more embodiments, I/O interface 940 can communicate or form networks via wireless communication.

One or more embodiments may be a computer program product. The computer program product may include a computer readable storage medium (or media) including computer readable program instructions for causing a processor to provide improved visualization/identification of structures within an eye during ophthalmic surgical procedures according to one or more embodiments described herein.

The computer readable storage medium is a tangible device that can retain and store instructions for use by an instruction execution device. The computer readable storage medium may be, for example, an electronic storage device, a magnetic storage device, an optical storage device, or other suitable storage media. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Program instructions, as described herein, can be downloaded to respective computing/processing devices from a computer readable storage medium or to an external computer or external storage device via a network, for example, the Internet, a local area network, a wide area network and/or a wireless network. A network adapter card or network interface in each computing/processing device may receive computer readable program instructions from the network and forward the computer readable program instructions for storage in a computer readable storage medium within the respective computing/processing device.

Computer readable program instructions for carrying out one or more embodiments, as described herein, may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on a single computer, or partly on the single computer and partly on a remote computer. In some embodiments, the computer readable program instructions may execute entirely on the remote computer. In the latter scenario, the remote computer may be connected to the single computer through any type of network, including a local area network (LAN) or a wide area network (WAN), or public network.

One or more embodiments are described herein with reference to a flowchart illustrations and/or block diagrams of methods, systems, and computer program products according to one or more of the embodiments described herein. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the method steps discussed above, or flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 10:
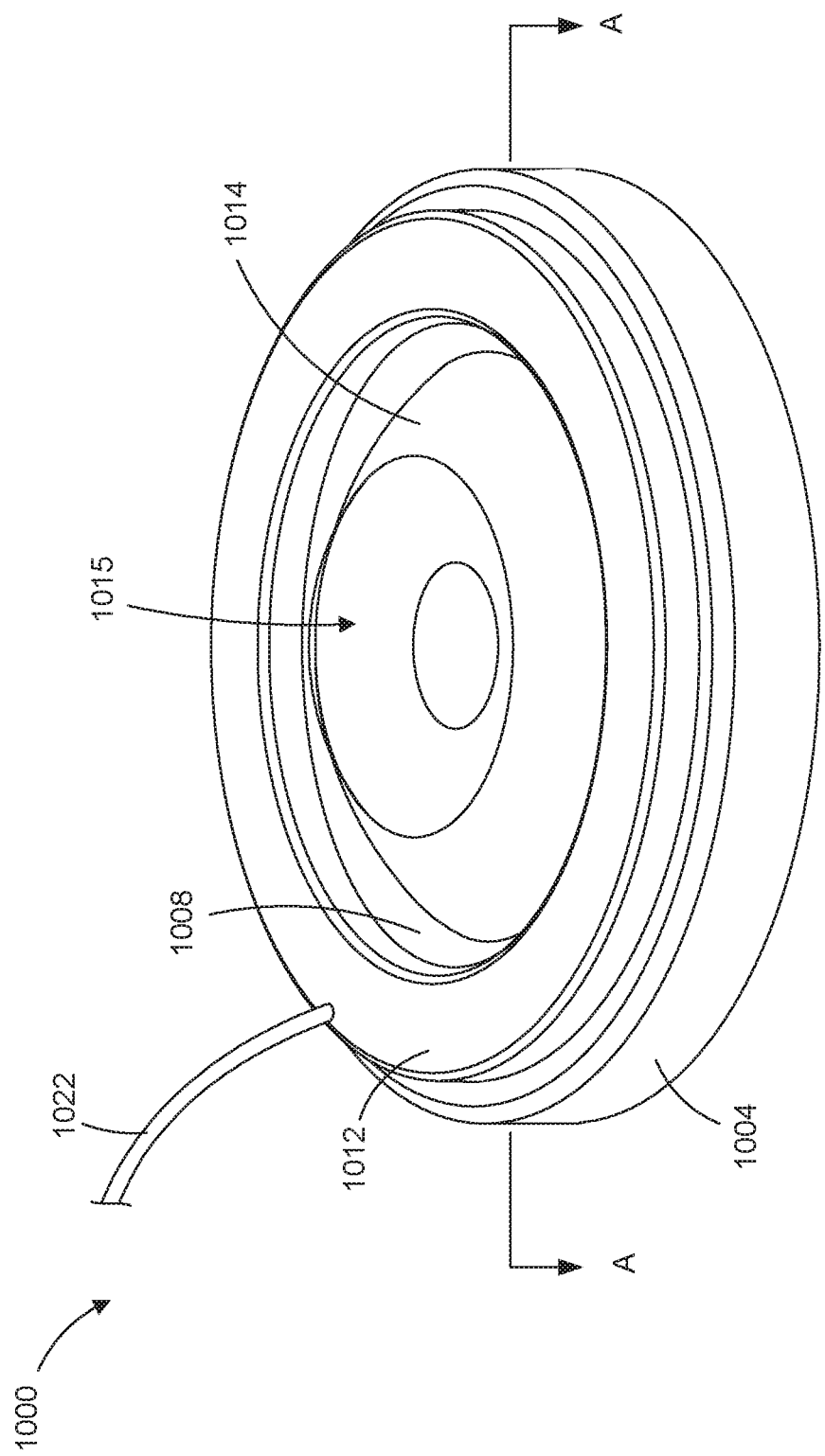
FIG. 10 depicts an ophthalmic surgical illumination device, according to one or more embodiments of the disclosure.
Figure 11:
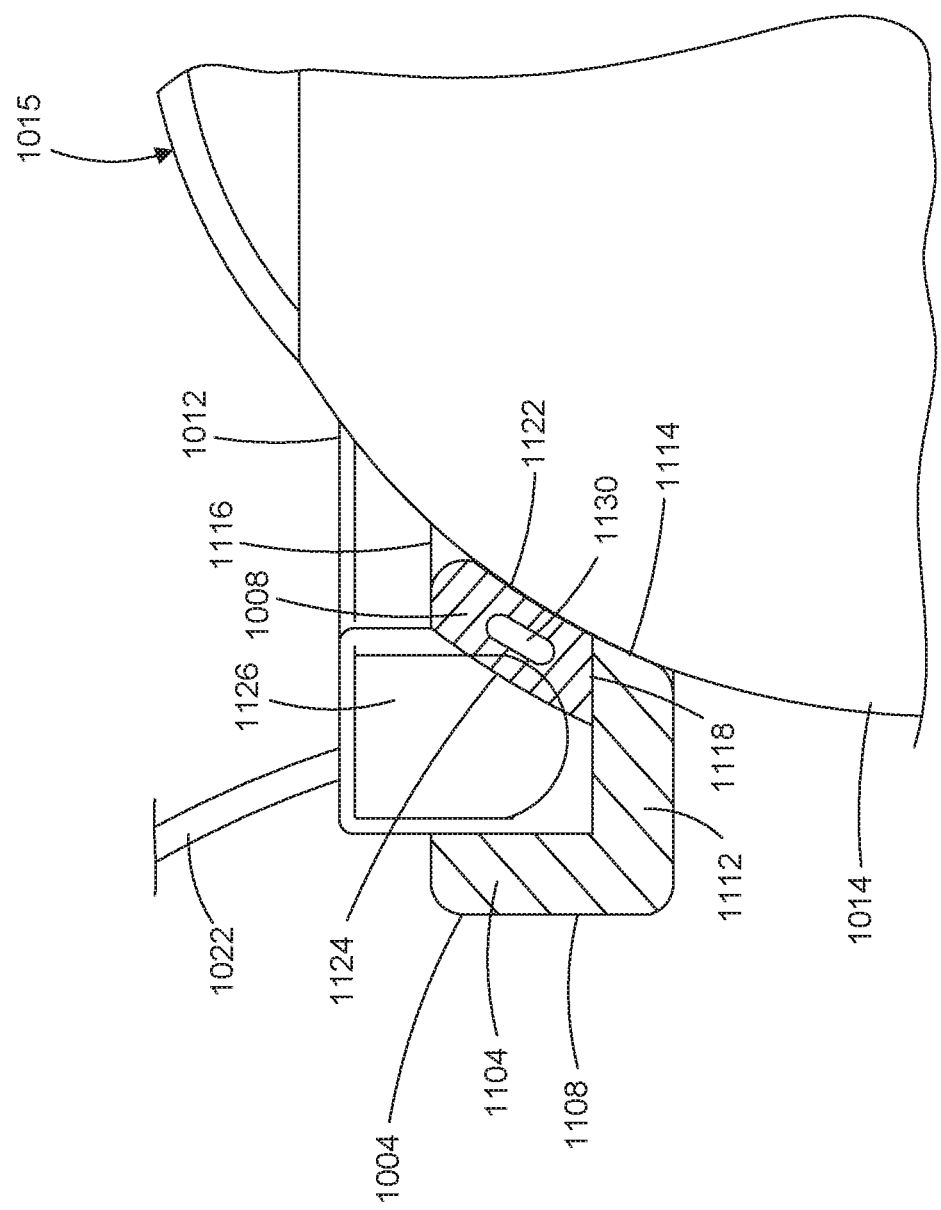
FIG. 11 depicts a cross-sectional view taken at line A-A of the illumination device of FIG. 10, according to one or more embodiments of the disclosure.

Referring to FIGS. 10-11 a perspective view and cross-sectional view of an ophthalmic illumination device 1000 is depicted, according to one or more embodiments of the disclosure. In one or more embodiments, the illumination device 1000 includes an annular base portion 1004, an annular scleral support 1008, and an annular illumination portion 1012. Depicted in FIGS. 10-11 the illumination device 1000 is configured to be placed on an eye 1014, for example resting on the sclera, with ring or annular shape of the illumination device 1000 exposing the central region 1015 of the eye 1014 through the annulus of the device 1000 such as for access to a surgeon.

Viewed in FIG. 11, in one or more embodiments the annular base portion 1004 has and L-shape with a first part of the L-shape defining an outward sidewall portion 1104 and outward sidewall 1108 and a second part of the L-shape and extending radially inwardly relative to the outward sidewall portion 1104 to define a floor portion 1112 and a radially inward sidewall 1114 that rests against the sclera when placed on an eye 1014. In various embodiments, the annular base portion is composed of plastic, silicone, or other suitable material for surgical procedures as known in the art.

In one or more embodiments, the annular scleral support 1008 has a generally frusto-conical shape that extends from a more radially inward top portion 1116 to a more radially outward bottom portion 1118 to form a shape that generally conforms to the curved shape of the eye 1014. In various embodiments the scleral support 1008 additionally includes an interior sidewall 1122 that rests on the conjunctiva above the peripheral sclera when placed on an eye 1014 and an exterior sidewall 1124. In one or more embodiments, the scleral support 1008 is assembled with the annular base portion 1004 at a radially most inward portion of the base portion 1004 to form a generally flush interior sidewall surface with the interior sidewall 1122 and the radially inward sidewall 1114 resting against the eye 1014. In one or more embodiments, the assembly defines an interior space or U-shaped region for placement of the annular illumination portion 1012. In various embodiments, the illumination portion 1012 is positioned such that it is adjacent to the scleral support 1008 but kept from direct contact with the eye 1014.

In various embodiments the annular illumination portion 1012 is piece of the device 1000 including one or more light emitting devices 1126 for illumination of the eye 1014. In various embodiments, the illumination portion 1012 is composed of a plastic ring with a plurality of near-infrared LEDS embedded therein and connected to a power source/control signal via cable 1022.

In one or more embodiments exterior sidewall 1124 of the scleral support 1008 includes a recess or groove for placement of the annular illumination portion 1012. Once in place the light from the embedded LEDs would illuminate the scleral and conjunctival surfaces with near-infrared light. In such embodiments the scleral support 1008 is composed of a clear or semi-clear material, such as silicone, plastic or other suitable surgical material that allows light from the illumination portion 1012 to pass through the support 1008 and illuminate the eye 1014. In one or more embodiments, the scleral support 1008 and/or other portions of the device are weighted such that the weight of the device mechanically blocks the outward flow of fluid through the aqueous veins when the device is placed on the eye 1014. By blocking flow, the aqueous veins will be slightly distended and easier to visualize using near infrared light while the device is in use.

In various embodiments, the scleral support can include one or more channels within the interior of the scleral ring with a plurality of ports in the interior sidewall 1122. In such embodiments, suction could be applied into the channel such that the silicone ring would be suctioned to the conjunctiva/sclera and form a firm seal against the eye to resist movement of the device and/or obtain good mechanical control of eye movement. Furthermore, additional blockage of flow through the aqueous draining veins could be obtained via a suction seal against the conjunctiva/sclera. In certain embodiments an open region 1130 is defined in the center of the silicone/plastic ring complex. In one or more embodiments the open region 1130 is a space that one or more other surgical devices. For example, in certain embodiments could include a prism used for parts of the surgery that require overcoming total internal reflection, viewing angle anatomy beyond the so-called critical angle.

In various embodiments, such as described above with reference to FIG. 7, the illumination device is incorporated as part of the overall imaging system 700. In such embodiments, the device 1000 can comprise at least the emitter portion of the system 700.

The method steps, flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some embodiments, the functions noted in the block may occur out of the order noted in the figures. For example, two blocks shown in succession may in fact, be executed substantially concurrently, or the blocks may sometimes be executed in the reverse order, depending upon the functionality involved.

In one or more embodiments, the program instructions of the computer program product are configured as an "App" or application executable on a laptop or handheld computer utilizing a general-purpose operating system. As such, in various embodiments can be implemented on a handheld device such as a tablet, smart phone, or other device.

In various embodiments the code/algorithms for implementing one or more embodiments are elements of a computer program product, as described above, as program instructions embodied in a computer readable storage medium. As such, such code/algorithms can be referred to a program instruction means for implementing various embodiments described herein.

The following patents and publications are incorporated herein by reference for all purposes: U.S. Pat. No. 6,276,798B1; US20020001080A1; US20180360655A1; US20080137034A1; US20170280989A1; U.S. Pat. No. 9,826,900B2; US20090225277A1; US20180360310A1; US20020013572A1; US20120184846A1; US20070191863A1; U.S. Pat. No. 8,230,866B2; CN104334072B; US20100134759A1; US20110213342A1; US20090254070A1; U.S. Pat. No. 9,675,244B1; U.S. Pat. No. 5,219,400A; US20040075812A1; U.S. Pat. No. 8,478,386B2; and U.S. Pat. No. 7,192,412B1.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system for surgical illumination and imaging of ophthalmologic structures within a human eye, said system comprising:
    an emitter configured to irradiate ophthalmologic structures with near infrared light;
    an imaging sensor configured to receive and detect near-infrared scatter from the irradiated ophthalmologic structures and visible light in real-time; and
    a system control and image processor device comprising a processor, an electronic storage location operatively coupled with the processor, a user display, and processor executable code stored on the electronic storage location and embodied in a non-transitory computer readable storage medium, the surgical microscope, emitter, and imaging sensor communicatively coupled together, the imaging sensor configured to transmit the detected near-infrared scatter and visible light to the system control and image processor device,
    wherein the processor executable code comprises machine-readable instructions, that when executed by the processor, causes an image to be displayed on the user display that indicates the irradiated ophthalmologic structures in real-time using the detected near-infrared scatter and a molar extinction coefficient correlated to photon absorption in the irradiated ophthalmologic structures.

2. The system of claim 1, wherein the ophthalmologic structures include one or more of a trabecular meshwork, a Schlemm's canal, an anterior chamber, and one or more aqueous veins.

3. The system of claim 1, wherein the image is a virtual image of the irradiated ophthalmologic structures generated at least based on near-infrared light scattering coefficients of the irradiated ophthalmologic structures.

4. The system of claim 1, wherein the system further comprises a surgical microscope.

5. The system of claim 4, wherein the image displayed on the user display includes the detected near-infrared scatter from the irradiated ophthalmologic structures overlaid on a real-time view from the surgical microscope.

6. The system of claim 4, wherein the emitter and camera are integrated into the surgical microscope.

7. The system of claim 1, wherein the user display comprises a heads-up display (HUD).

8. The system of claim 1, wherein the system further comprises a projector and the near infrared eye image is projected onto eye.

9. The system of claim 1, wherein the emitter comprises:
    an annular base portion, the annular base portion having an L-shape with a first part of the L-shape defining an outward sidewall portion and outward sidewall and a second part of the L-shape extending radially inwardly relative to the outward sidewall portion to define a floor portion and a radially inward sidewall that rests against the sclera when placed on an eye;
    an annular scleral support having a generally frusto-conical shape that extends from a more radially inward top portion to a more radially outward bottom portion, the scleral support having an interior sidewall that rests on against a sclera when placed on an eye and an exterior sidewall, the scleral support assembled with the annular base portion at a radially most inward portion of the base portion to form a generally flush interior sidewall surface with the interior sidewall and the radially inward sidewall resting against the eye;
    an annular illumination portion includes one or more light emitting devices embedded therein and connected to a power source/control signal via a cable, wherein the assembled annular base portion and scleral support defining an interior space for placement of an annular illumination portion;
    wherein, the scleral support is composed of a clear or semi-clear material and wherein in operation light emitted from the embedded light emitting devices illuminate or transilluminate tissue of the eye.

10. The system of claim 9, wherein exterior sidewall of the scleral support includes a recess or groove for placement of the annular illumination portion.

11. A surgical illumination device for ophthalmologic structures configured to be placed on an eye, the device comprising:
    an annular base portion, the annular base portion having an L-shape with a first part of the L-shape defining an outward sidewall portion and outward sidewall and a second part of the L-shape extending radially inwardly relative to the outward sidewall portion to define a floor portion and a radially inward sidewall that rests against the sclera when placed on an eye;
    an annular scleral support having a generally frusto-conical shape that extends from a more radially inward top portion to a more radially outward bottom portion, the scleral support having an interior sidewall that rests on against a sclera when placed on an eye and an exterior sidewall, the scleral support assembled with the annular base portion at a radially most inward portion of the base portion to form a generally flush interior sidewall surface with the interior sidewall and the radially inward sidewall resting against the eye;
    an annular illumination portion includes one or more light emitting devices embedded therein and connected to a power source/control signal via a cable, wherein the assembled annular base portion and scleral support defining an interior space for placement of an annular illumination portion;

wherein, the scleral support is composed of a clear or semi-clear material and wherein in operation light emitted from the embedded light emitting devices illuminate or transilluminate tissue of the eye.

12. The surgical illumination device of claim 11, wherein exterior sidewall of the scleral support includes a recess or groove for placement of the annular illumination portion.

13. The surgical illumination device of claim 11, wherein one or more portions of the device are weighted such that the weight of the device mechanically blocks the outward flow of fluid through the aqueous veins when the device is placed on the eye.

14. The surgical illumination device of claim 11, wherein the scleral support includes one or more channels within the interior of the scleral ring with a plurality of ports in the interior sidewall.

15. The surgical illumination device of claim 11, wherein the scleral support includes an interior open space for placement of various surgical devices.

16. The surgical illumination device of claim 11, wherein a prism is positioned in the interior open space.

17. A method of surgical imaging comprising:
providing the system of claim 1;
irradiating, via the emitter, ophthalmologic structures with near infrared light;
detecting, via the imaging sensor, near-infrared scatter from the irradiated ophthalmologic structures and visible light in real-time; and
generating in real-time via the system control and image processor device, an image to be displayed on the user display that includes the detected near-infrared scatter from the irradiated ophthalmologic structures displayed in real-time.

18. The method of claim 17, further comprising:
displaying a view from the surgical microscope on a heads-up display (HUD).

19. The method of claim 17, further comprising:
displaying the near infrared image of the eye on a HUD.

20. The method of claim 18, further comprising:
overlaying the generated image on the view from the surgical microscope.

* * * * *